(12) United States Patent
Tatsumi et al.

(10) Patent No.: US 10,888,252 B2
(45) Date of Patent: Jan. 12, 2021

(54) SCAPULAE POSITION MEASURING DEVICE AND METHOD

(71) Applicant: Maido Co. Ltd., Amagasaki (JP)

(72) Inventors: Hiroyuki Tatsumi, Amagasaki (JP); Tomoko Maekawa, Amagasaki (JP)

(73) Assignee: Maido Co. Ltd., Amagasaki (JP)

( * ) Notice: Subject to any disclaimer, the term of this patent is extended or adjusted under 35 U.S.C. 154(b) by 148 days.

(21) Appl. No.: 16/150,867

(22) Filed: Oct. 3, 2018

(65) Prior Publication Data

US 2019/0029568 A1    Jan. 31, 2019

Related U.S. Application Data

(62) Division of application No. 14/682,025, filed on Apr. 8, 2015, now abandoned.

(30) Foreign Application Priority Data

Apr. 9, 2014    (JP) .................................. 2014-80116

(51) Int. Cl.
   *A61B 5/107*    (2006.01)
   *A61B 5/11*    (2006.01)
   *A61B 5/00*    (2006.01)

(52) U.S. Cl.
   CPC .......... *A61B 5/1116* (2013.01); *A61B 5/1072* (2013.01); *A61B 5/4504* (2013.01); *A61B 5/4576* (2013.01); *A61B 5/1127* (2013.01); *A61B 5/4519* (2013.01); *A61B 2503/10* (2013.01)

(58) Field of Classification Search
   CPC .................................................. A61B 5/1072
   See application file for complete search history.

(56) References Cited

U.S. PATENT DOCUMENTS

2,063,922 A * 12/1936 Greenberg ............... A41H 1/02
                                                33/2 R
2,137,583 A    11/1938 Orvold

FOREIGN PATENT DOCUMENTS

JP    H02102641 A    4/1990
JP    H10234710 A    9/1998

OTHER PUBLICATIONS

US Patent and Trademark Office; Office Action for U.S. Appl. No. 14/682,025 dated Jan. 22, 2018.
US Patent and Trademark Office; Final Office Action for U.S. Appl. No. 14/682,025 dated Jul. 3, 2018.

* cited by examiner

*Primary Examiner* — Samuel S Hanna
(74) *Attorney, Agent, or Firm* — Parsons Behle & Latimer (57) ABSTRACT

A scapulae position measurement device and method includes a main body extending in the vertical direction, configured to be positioned to run along the spinal column, having a vertical scale, and a moveable arm, extending in a horizontal direction on the right or left side of the main body, having a horizontal scale. The scapulae position measurement device is capable of measuring position changes of the horizontal direction (X axis) and vertical direction (Y axis) of the scapulae, and capable of displaying the tension/relax state of the surrounding muscles of the scapulae with an objective numerical value.

4 Claims, 11 Drawing Sheets

FIG. 14

SCAPULAE POSITION MEASURING DEVICE AND METHOD

CROSS REFERENCE TO RELATED APPLICATIONS

The present application is a divisional of U.S. patent application Ser. No. 14/682,025 filed on Apr. 8, 2015, and entitled "SCAPULAE POSITION MEASURING DEVICE AND METHOD," which claims the benefit of Japanese Patent Application Serial No. 2014-80116, entitled "SHOULDER BLADE POSITION MEASUREMENT INSTRUMENT AND SHOULDER BLADE POSITION MEASUREMENT METHOD," filed on Apr. 9, 2014, the disclosures of each being hereby incorporated by reference in their entirety.

FIELD OF THE DISCLOSURE

The present disclosure relates to a scapulae position measurement device and a scapulae position measurement method capable of measuring the therapeutic effects for stiff shoulders and poor posture caused by the malposition of the scapulae, using an objective numerical value.

BACKGROUND

In recent years, there has been an increase in the number of people complaining about "stiff shoulders," which is accompanied by stiffness, pain and even headaches or nausea when the neck, shoulders and back are stretched. According to the 2010 National Life Infrastructure survey of the Japanese Ministry of Health, Labor and Welfare, the percentage of stiff shoulders have become the No. 2 complaints in men and No. 1 in women. The factors of why this issue has been increasing is due to bad posture, such as stooping and slouching caused by the rapid spread of Smartphones, or the like, and increase in computer use at the workplace, lack of exercise, work in a posture where the neck and shoulders are tense and maintain the same poor posture continuously, not to mention the fatigue already cause by too much air conditioning and mental stress.

When there is a "stiff shoulders" posture as described above, the scapulae in the dorsal part are often shifted upward and outward from their correct position. The scapulae are thin, palm-sized bones found at the back of the human body. The scapulae consist of two bones, one on the left and one on the right. Since the scapulae are floating at the back of the ribs, multiple muscles which are attached to the lower and upper part, left and right surface and back side of the scapulae are supporting the scapulae. The muscles which are attached to the scapulae are used not only to move the arms and shoulders, but also connect the ribs to help the respiratory process, support the head when moving the neck etc., and several related movements of the body. Due to changes in the muscle balance caused by muscle tension and loose muscle which is connected to the scapulae, even with a simple gesture of extending the arm or tilting the head, the scapulae will eventually change its position.

Since the scapulae are floating at the back of the ribs without being in contact with any other bones, the position of the scapulae will depend on the tense state of the muscle groups which are attached to the scapulae even when the body is not in motion. The balance between each muscle can be out of control and the scapulae can be shifted from its position because the posture is in a bad position in which the muscle groups around the scapulae are under excessive tension and loose more than they should be. Especially in a condition called stiff shoulder, there are lots of cases whereby the scapulae has shifted from the correct position to the upward and outward side, and rotating upward (upper part of the scapulae will be close to the spine, and the lower part of the scapulae will be rotating outward away from the spine).

The Japanese Orthopaedic Association has noted that the trapezius muscle, levator scapulae muscle, rhomboid major muscle, rhomboid minor muscle, supraspinatus muscle, semispinalis capitis, splenius capitis muscle and splenius cervicis muscle are the muscles which are related to "stiff shoulders." In particular, the trapezius muscle and levator scapulae muscle are both referred to as the stiff shoulder line, and there are often cases whereby the tension of these causes stiff shoulders. Scapulae in the stiff shoulder state are being pulled upward by the tension of the trapezius muscle and the levator scapulae muscle, and then are in an upward rotation condition after it has been shifted outward by the loosening of the rhomboid muscle.

There are many healthcare methods for improving and treating stiff shoulders, such as massage therapy, hyperthermia therapy, exercise therapy, rest therapy, drug therapy, acupuncture, etc. From these methods, when the muscle tension of the muscle groups around the scapulae is relaxed and the scapulae has returned back to its proper position, the stiff shoulders from posture such as stoop and slouch will be improved and the stiff shoulders symptom will be prevented as well. The stiff shoulders improvement methods described above have been conducted by qualified personnel not only at orthopedic clinics, rehabilitation centers, orthopedic hospitals, acupuncture hospitals, and massage centers by a masseuse, but even at various types of private facilities such as sports clubs, trainers, and manipulative therapy centers.

SUMMARY

Even in fields such as medical care and private hospitals, however, there is little consideration to effectiveness of treatment after deploying the position measurement of the scapulae. Even at an orthopedic clinic, the diagnosis of stiff shoulders, such as by verification of the existence of pain pressure and muscle tension at the trapezius muscle using the palpation method, and checking on possible movement in areas connected to the shoulders and verification of the cervical spine disease, is common. Hence, there has been a request to present the re-conditioning of the scapulae by using an objective numerical value.

The device and method of the present disclosure was made in view of such technical background, and the purpose is to provide a scapulae position measurement device and scapulae position measurement method which use an objective numerical value for the effective treatment of stiff shoulders and poor posture caused by the malposition of the scapulae.

The present disclosure provides a scapulae position measurement device which comprises a main body extending in the vertical direction and an arm extending in at least the right or left direction from said main body. The main body is arranged to the spine in a predetermined location, and the arm is changed to the position along the main body to fit the height position of the predetermined location of the right or left scapulae. The position of the horizontal direction for the right or left scapulae is measured by measuring the position of the predetermined location for the right or left scapulae to the arm and the position of the vertical direction for the right or left scapulae is measured by measuring the position of the arm to the main body. According to this, it is possible to easily and accurately measure the positions in the horizontal direction and the position in the vertical direction of the right or left scapula.

The device of the present disclosure may be configured such that the scale of the vertical direction is provided on the main body, and the scales of the right direction and left direction are provided on the respective arm(s), wherein the position of the horizontal direction for the right or left scapula can be measured by measuring the position of a predetermined location of the right or left scapula facing the arm with the scale of the arm, and the position of the vertical direction of the right or left scapulae can be measured by measuring the position of the arm facing the main body with the scale of the arm. According to this, by simplifying the structure, the horizontal and vertical position of the right or left scapulae can be determined easily as an objective numerical value.

The device of the present disclosure may be configured such that a positional measurement device can be provided on the main body or arm, and the position of the horizontal direction for the right or left scapulae can be measured by measuring the position of a predetermined location for the right or left scapulae, facing the arm, with the positional measurement device, and the position of the vertical direction of the right of left scapulae can be measured by measuring the position of the arm, facing the arm, with the positional measurement device. The positional measurement device can use laser and/or ultrasound to measure the distance, and measures the position by electrical, optical or ultrasonic methods. According to this, by carrying out the electrical, optical or ultrasonic method, the position in the horizontal direction of the right or left scapulae and the position of the vertical direction can be measured accurately with the objective numerical value.

The device of the present disclosure maybe configured to have a measurement value display part for displaying the measurement value of the position of the horizontal direction and/or vertical direction at the right or left scapulae measured by the positional measurement device. According to this, users can easily grasp the horizontal direction position and vertical direction position of the right or left scapulae by verifying the measurement value display part of the positional measurement device.

The device of the present disclosure may be configured such that the arm is provided so as to be capable of sliding in the vertical direction of the main body. According to this, the arm is allowed to slide in the vertical direction of the main body and the position can be changed so that it would fit to the predetermined height position of the right and/or left scapulae.

The device of the present disclosure may be configured such that the arm is provided so as to be able to slide in the vertical direction of the main body by fitting the ridges extending in a vertical direction that are provided on the main body or arm with the grooves extending in the vertical direction that are provided on the arm or the main body. According to this, the arm is allowed to slide in the vertical direction of the main body with a simple structure, and the position can be changed so that it would fit to the predetermined height position of the right and/or left scapulae.

The scapulae position measurement device maybe configured such that the main body includes a fall-prevention device to prevent the bar from falling by locking the arm when the arm is sliding. According to this, when sliding the arm, it can prevent falling from falling off the end of the main body.

In addition, the arm may be detachable from the main body. According to this, the scapulae position measurement device can disassemble into various parts for compact storage or to make it portable.

Further, the arm may be detachably connected to the main body using a magnet. According to this, the arm can easily be detached from or attached to the main body of the scapulae position measurement device.

The arm may be configured to have a bar indicator member that slides in the right or left direction. This provides an indicator member for the arm that is capable of being displaced to the appointed area of the right scapulae or the left scapulae. The horizontal position of the right scapulae or the horizontal position of the left scapulae is measured by measuring the position of indicator member on the arm. According to this, the position of the horizontal direction of the right and/or left scapulae can be measured accurately.

Further, the main body may be configured to have a main body indicator member that slides in a vertical direction. This provides an indicator member that is capable of indicating a vertical position of the right scapulae or the vertical position of the left scapulae by measuring the position of the main body indicator member for the respective arm. According to this, the position of the vertical direction of the right and/or left scapulae can be measured accurately.

Furthermore, the main body may be made from flexible bending materials in the thickness direction. According to this, even when the test subject is a person whose back is bent due to an incident such as traffic accident, the main body of the scapula measurement device can be bent to follow the curvature of the spine. Due to this, even when the test subject is a person whose back is bent, the predetermined direction position of the scapulae can be measured.

Moreover, the scapulae position measurement method of the present disclosure comprises a main body of a form extending in the vertical direction, and an arm provided in a form extending in the right and left direction for the main body, wherein the main body of the scapulae position measurement device is positioned in a predetermined location along the spine and the arm is repositioned at the main body to fit the height/vertical position of a predetermined location of the right or left scapulae. The position of the horizontal direction for the right or left scapulae is measured by measuring the position of the predetermined location for the right or left scapulae relative to the arm, and the position of the vertical direction for the right or left scapulae is measured by measuring the position of the arm relative to the main body.

According to this, it is possible to easily and accurately measure the positions of the horizontal direction and the predetermined vertical direction position of the right or left scapulae.

According to the present disclosure, the change in position of the horizontal direction and vertical direction of the scapulae can be measured, and it is possible to present the tension and/or the relaxed state of the muscles surrounding the scapulae with an objective numerical value. With this treatment, which allows the muscles surrounding the scapulae to be represented by an objective numerical value, it becomes possible to provide specific treatment to patients.

In addition, the device of the present disclosure can be disassembled into various parts for compact storage.

Also, the scapulae position measurement device, which measures a change in position of the scapulae for therapeutic purposes, can also be used for proactive applications in other areas, such as sports and beauty. By measuring the increase and/or decrease in the movable range of the scapulae, this objective measurement can be applied to performance in sports, posture, and cosmetic appearance. There are many imaginable uses that fall under a wide range of applications.

DETAILED DESCRIPTION

Figure 1:
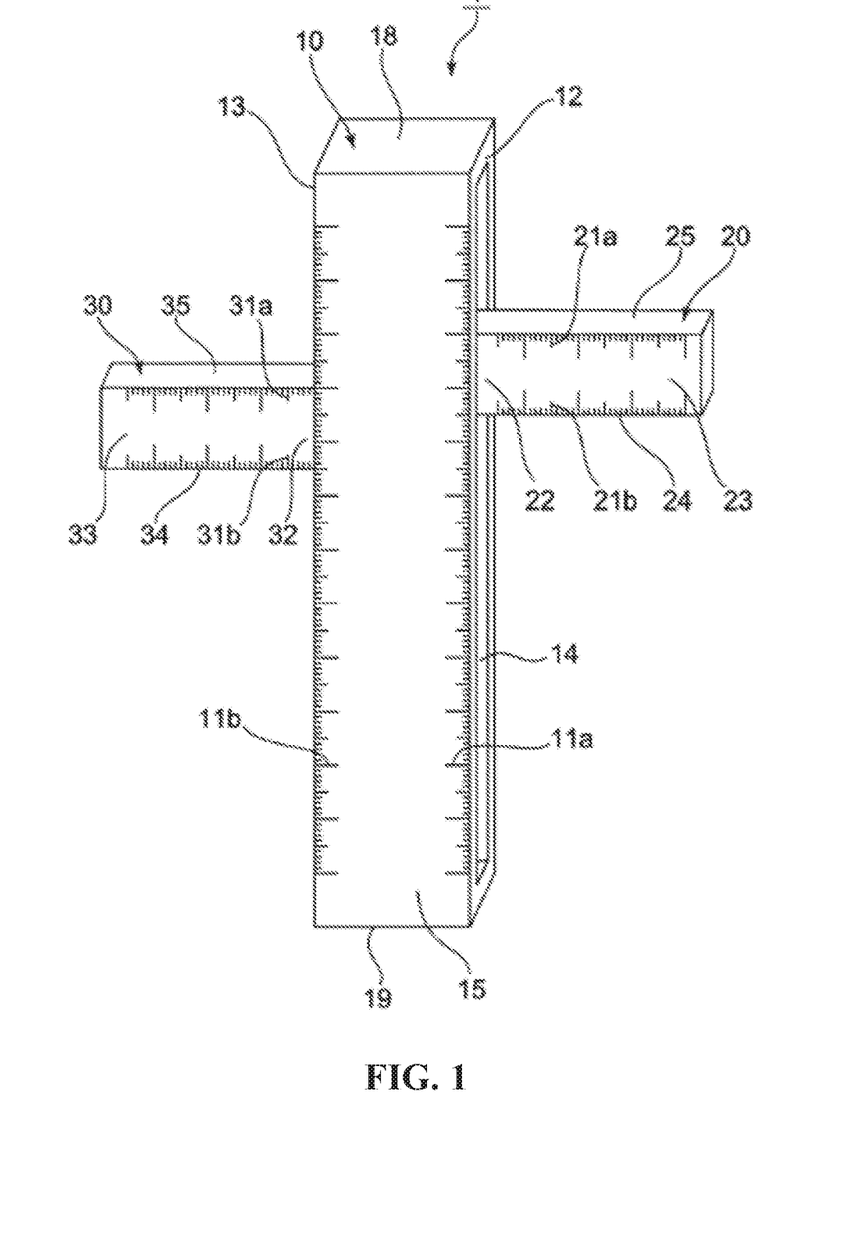
FIG. 1 is a perspective illustration showing an embodiment of a scapulae position measurement device according to the present disclosure.
Figure 2:
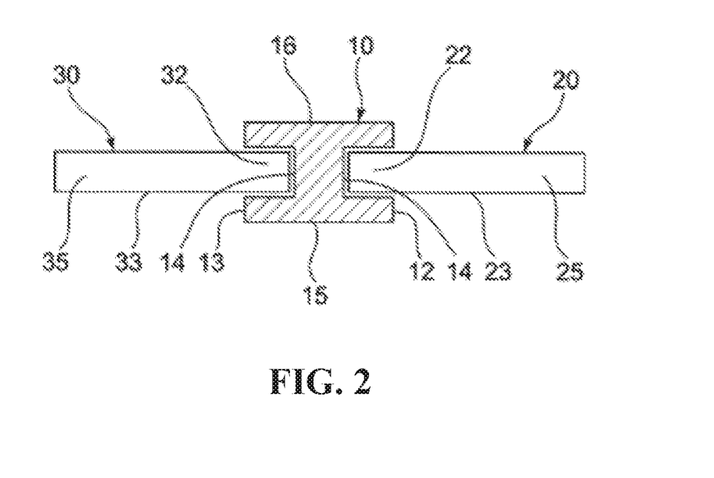
FIG. 2 is a transverse section of the scapulae position measurement device of FIG. 1.
Figure 3:
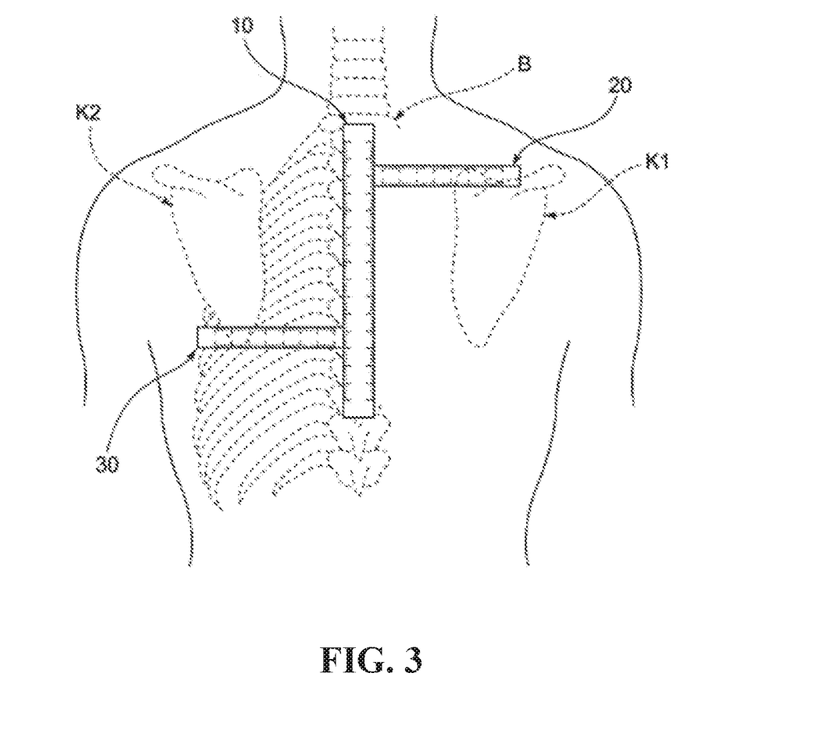
FIG. 3 is a front elevation view, showing the usage of the scapulae position measurement device.

Shown in FIGS. 1-3 is an embodiment of a scapulae position measurement device according to the present disclosure. In the description below, the horizontal direction is set to the X axis and the vertical direction is set to the Y axis of the human body.

As shown in FIG. 1, the scapulae position measurement device 1 comprises a main body 10 having a scale 11a and 11b in the vertical direction, a right arm 20 on the right side of the main body 10, having a scale 21a and 21b in the horizontal direction, and a left arm 30 provided on the left side of the main body 10, having a scale 31a and 31b in the horizontal direction.

The main body 10 is a rectangular pillar which can be aligned in the vertical direction. A groove 14 is provided in the main body 10, which extends in the vertical direction (length direction) of the main body 10 at the right side of the surface part 12 and left side of the surface part 13. This groove 14 is linearly provided with the main body 10 from the top to the bottom in a constant width and constant depth. The main body 10 is provided with a scale 11a of the vertical direction at the right side of the front surface 15, and a scale 11b of the vertical direction at the left side of the front surface 15. These scales 11a and 11b can be made longer than the length of the vertical dimension of the typical human scapulae. Specifically, the scales 11a and 11b can have a length of about 20-50 cm.

The right arm 20 is a rectangular pillar which is provided in a horizontal extending form in the right direction of the main body 10. The right arm 20 has a left edge part 22 fitted to the groove 14 of the main body 10 and it can have a size and shape to slide in the vertical direction. In addition, the right arm 20 can be provided with a scale 21a of the horizontal direction at the upper side of the front surface 23, and scale 21b of the horizontal direction at the lower side of the front surface 23. These scales 21a and 21b are made to be longer than the length from the spinal column B of a normal human being up to a predetermined location (e.g. upper corner, lower corner) of the scapulae K1. Specifically, the scales 21a and 21b can have a length of about 20-50 cm. In addition, the right side of the arm can be made to be longer than the length up to half the width of the back (the width between the base of the left and right arms) of a normal human body. Specifically, the right side of the arm can have a length of about 30-60 cm.

As shown in FIG. 2, the right arm 20 can be slid upward with the left edge of part 22 to the groove 14, to a position where the upper surface 25 of the right arm 20 matches the height position of the upper corner of the right scapula K1. Then, the position of the X axis in the upper corner of the right scapulae K1 can be measured by measuring the position in the upper corner of the right side of the scapulae K1 with the scale 21a, and the position of Y axis in the upper corner of the right scapulae K1 can be measured by measuring the position in the vertical direction of the right arm 20 with the scale 11a on the main body 10.

Also, the left arm 20 can be slid downward with the left edge part 22 in the groove 14, to a position where the lower surface 24 of the right arm 20 matches the height position of the lower corner of the right scapulae K1. Then, the position of the X axis in the lower corner of the right scapulae K1 can be measured by measuring the position in the lower corner of the right side of the scapulae K1 with the scale 21b, and the position of Y axis in the lower corner of the right scapulae K1 can be measured by measuring the position in the vertical direction of the right arm 20 with the scale 11a on the main body 10.

On the other hand, the left arm 30 is a rectangular pillar which is horizontally provided in an extending form in the left direction of the main body 10. The left arm 30 has a right edge part 32 fitted to the groove 14 of the main body 10 and can have a size and shape capable of sliding in the vertical direction. The left arm 30 can have the scale 31a of the horizontal direction at the upper side of the front surface 33, and the scale 31b of the horizontal direction at the lower side of the front surface 33. These scales 31a and 31b can have a length that is longer than the length from the spinal column B of a typical human up to a predetermined location (e.g. upper corner, lower corner) of the scapulae K2. Specifically, the scales 31a and 31b can have a length of about 20-50 cm. In addition, the left side of the arm 30 can have a length longer than the length up to half the width of the back (the width between the base of the left and right arms) of the general human body. Specifically, the left side of the arm can have a length of about 30-60 cm.

As shown in FIG. 2, the left arm 30 can be slid upward with the right edge part 32 to the groove 14, to a position on the upper surface 35 at the left arm 30 to match the height position of the upper corner of the left scapulae K2. Then, the position of the X axis in the upper corner of the left scapulae K2 can be measured by measuring the position in the upper corner with the scale 31a, and the position of the Y axis in the upper corner of the left scapulae K2 can be measured by measuring the position in the vertical direction in the left arm 30 with the scale 11b on the main body 10.

Similarly, the left arm 30 can be slid downward with the right edge part 32 in the groove 14, and then the lower surface 34 at the left arm 30 can be changed to the position to match the height position of the lower corner of the left scapulae K2. Then, the position of the X axis in the lower corner of the left scapulae K2 is measured by measuring the position in the lower corner with the scale 31b, and the position of the Y axis in the lower corner of the left scapulae K2 can be measured by measuring the position in the vertical direction of the left arm 30 with the scale 11b on the main body 10.

Next, the description will be on the usage of the scapulae position measurement device 1. As shown in FIG. 3, first, the users will bring the back surface 16 of the main body into contact to the back of the test subject and then align the main body 10 together with the spinal column B. During this time, the main body and the spinal column B are preferably arranged in the same predetermined location whereby the top edge part of the main body 10 will match the predetermined location.

Next, users will change the position on the right arm 20 to the position in the vertical direction of the upper corner of the right scapulae K1. Specifically, the user will slide the right arm 20 upward with the fitting form at the left edge part 22 to the groove 14, and then the right arm 20 at the upper surface 25 will be changed to the position to match the height position of the upper corner of the right scapulae K1. Then, the user will measure the position of the X axis in the upper corner of the right scapulae K1 by measuring the position in the upper corner with the scale 21a, and will measure the position of Y axis in the upper corner of the right scapulae K1 by measuring the position of the vertical direction at the right arm 20 with the scale 11a on the main body 10.

Similarly, users will change the position for the right arm 20 to the position of the vertical direction of the lower corner of the right scapulae K1. Specifically, the user will slide the right arm 20 downward with the fitting form at the left edge part 22 to the groove 14, and then the right arm 20 at the lower surface 24 will be changed to the position to match the height position in the lower corner of the right scapulae K1. Then, the user will measure the position of the X axis in the lower corner in the right scapulae K1 by measuring the position in the lower corner with the scale 21b, and measure the position of the Y axis in the lower corner of the right scapulae K1 by measuring the position of the vertical direction at the right arm 20 with the scale 11a on the main body 10.

Next, users will change the position for the left arm 30 to the position of the vertical direction of the upper corner of the left scapulae K2. Specifically, the user will slide the left arm 30 upward with the fitting form at the right edge part 32 to the groove 14, and then the left arm 30 at the upper surface 35 will be changed to the position to match the height position of the upper corner of the right scapulae K2. Then, the user will measure the position of the X axis in the upper corner of the left scapulae K2 by measuring the position in the upper corner with the scale 31a, and measure the position of the Y axis in the upper corner of the left scapulae K2 by measuring the position in the vertical direction at the left arm 30 with the scale 11b on the main body 10.

Similarly, users will change the position on the left arm 30 to the position of the vertical direction in the lower corner of the right scapulae K2. Specifically, the user will slide the left arm 30 downward with the fitting form at the left edge part 32 to the groove 14, and then the left arm 30 at the lower surface 34 will be changed to the position to match the height position of the lower corner of the left scapulae K2. Then, the user will measure the position of the X axis in the lower corner of the left scapulae K2 by measuring the position in the lower corner with the scale 31b, and measure the position of Y axis in the lower corner of the left scapulae K2 by measuring the position of the vertical direction at the left arm 30 with the scale 11b on the main body 10.

Then, the user can place the spinal column B along the Y axis and the X axis in the spinal vertical line, and then, the position of the left and right scapulae K1 and K2 can be measured. The measurement point is being configured for the upper corner (upper part of the corner inside the scapulae) inside the scapulae K1 and K2, and the lower corner (lower corner of the scapulae) inside the lower part of the same scapulae. There are no issues with using the measurement point at places besides scapulae K1 and K2 (for example, scapular spine). However, the upper corner and lower corner were not only easy to be palpated, but also they have an end part of the muscles which is related to the measurement.

The positional change of the horizontal direction from the spinal column B of the left and right upper or lower corner, which is the inside corner of scapulae K1 and K2, is measured with the X-axis, and the positional change of the vertical direction from the spinal column B of the upper or lower right and left scapulaes K1 and K2, is measured with the Y-axis. According to this, it is possible to measure the changes on the X and Y axis on the left and right scapulae. In addition, it is possible to verify the changes of the X and Y axis for the left and right scapulae K1 and K2 respectively.

The reason for measuring the changes in X axis is because of the scapulae K1 and K2 are separated from the spinal column B and spread outwardly when the back is rounded to lean forward (aversion of the scapulae). At this time, rhomboid major and minor muscles which are related to the stiff shoulders will be stretched and the distance from the spinal column B of the scapulae K1 and K2 becomes wider. The rhomboid major and minor muscles are adductor muscles which are pulled to the spinal column B of the scapulae K1 and K2. In addition, since the trapezius muscle is the stiff shoulder muscle, downward rotation (a movement which is rotating the scapulae so that the lower corner will be approaching the inside) of the opposite movement of the scapulae K1 and K2 are also being carried out. The rhomboid major and minor muscles will easily relax when the trapezius muscle is tense. The rhomboid minor muscle starts from the spinous process of the cervical vertebrae C6-C7 (cervical vertebrae C7 sliding the thoracic T1), and ends at the internal top part of the scapulae. The rhomboid major muscle starts from the spinous process of the thoracic vertebrae T1-T4, and ends at the internal bottom part of the scapulae. The rhomboid major and minor muscles are used, for example, when pulling a drawer to the front, and if the rhomboid major and minor muscles are in a relaxed condition whereby they are away from the spinal column B such as when the scapulae is barely near to the hand to reach until the position whereby the hand is extended, they will be located outside the disposition. Thus, the position changes at the upper corner and lower corner of the X axis for the scapulae K1 and K2 have appeared to change the position of the tension and/or relaxing state and inward (adduction)

and/or outward (abduction) of the rhomboid major and minor muscles, trapezius muscle and levator scapulae muscle.

The reason for measuring the changes in Y axis is because the upper corner of the scapulae is increasing on the spine when the shoulders are in the elevated (e.g. shrugging) condition, whereby the head is falling to the front.

At this time, the levator scapulae muscle which is related to stiff shoulder is in a tension state by pulling up the upper corner of the scapulae, and the position of the scapulae K1 and K2 on spinal column B will be changed upwardly. Since the levator scapulae muscle together with the trapezius muscle are using the scapulae for raising activities (on the levator scapulae muscle), then both of these muscles are similarly tense during the tension state. The levator scapulae muscle starts from the nodules after the spinous process of the cervical vertebrae C1-C4, and ends at the related inside and upper corner on the top part of the scapulae. The levator scapulae muscle together with the trapezius muscle are used when shrugging the shoulders and also when lifting things. If the levator scapulae muscle is in tension, such as when the scapulae K1 and K2 are being pulled up, shrugging the shoulders, they will move to the upward direction on the spinal column B. Thus, the position changes at the upper corner of Y axis for the scapulae K1 and K2 have appeared to change the position of the tense muscle and/or relaxing state and upward (elevation) and/or downward (under the system) of the levator scapulae muscle.

Furthermore, by measuring the position changes on the X axis and Y axis of the upper corner and lower corner of the scapulae K1 and K2, it becomes possible to also measure the rotation state of the scapulae K1 and K2. In addition, by measuring the changes on the X axis and Y axis of the scapulae K1 and K2, not only for the rhomboid major and minor muscles, but also for the trapezius muscle and levator scapulae muscle which have been described above, it is possible to estimate the condition of the synergist and antagonistic muscle (muscles which are moving in an opposite way). By measuring the changes of the upper corner and lower corner of the scapulae K1 and K2, it can be understood that the tension and/or relaxed state for all of the muscle groups are moving in the position of the scapulae K1 and K2.

As described above, by finding the extension of the straight line and the intersection of the Y axis which is connected to the position of the upper corner and lower corner of the scapulae K1 and K2, it becomes possible to find the position of the scapulae at the angle, and the tense and/or relaxed state of the muscles surrounding the scapulae K1 and K2 can be measured with an objective numerical value. From there, the effect of treatment to the surrounding muscles of the scapulae K1 and K2 can be detected by using the objective numerical value, and not only is it possible to present the specific treatment effect to the patients and customers, but also, the numerical value can be applied to a computer program on health maintenance, exercise and rehabilitation.

This kind of scapulae position measurement device can independently change the position between the right arm 20 and left arm 30. Due to this, the position of the right scapulae K1 and the position of the left scapulae K2 can be measured at the same time from the right arm 20 and the left arm 30, and it becomes possible to improve the measurement efficiency.

Figure 4A:
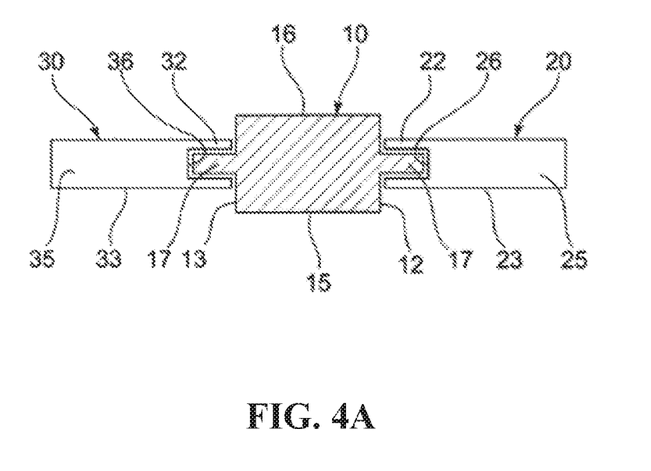
FIGS. 4A and 4B are transverse sections showing alternative embodiments of the scapulae position measurement device of FIG. 1.

In another embodiment, shown in FIG. 4A, the scapulae position measurement device 1 is provided with a projection 17 from the upper part to the bottom part of the main body 10, whereby the projection 17 extends in the vertical direction at the right side surface 12 and the left side surface 13 of the main body. The groove 26 and 36 which fit with the projection 17 are provided at the right arm 20 and the left arm 30.

Figure 4B:
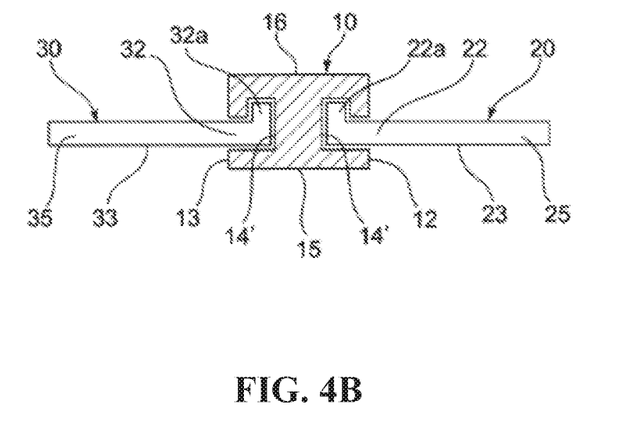

In another embodiment, shown in FIG. 4B, the scapulae position measurement device 1 is provided with a hook-shaped groove 14 from the upper part to the bottom part of the main body 10, whereby the groove 14 extends in the vertical direction at the right side surface 12 and left side surface 13 of the main body. At the left edge part 22 of the right arm 20 and the right edge part 32 of the left arm 30, the hook-shaped groove 14 and the fitting bent parts 22a and 32a are provided.

Another embodiment of a scapulae position measurement device 1 of the present disclosure will be described while referring to FIG. 5 and FIG. 6. Only the configuration differing from the above embodiments will be described, whereby descriptions of like configurations will be omitted, and like components are indicated by corresponding reference numerals.

Figure 5:
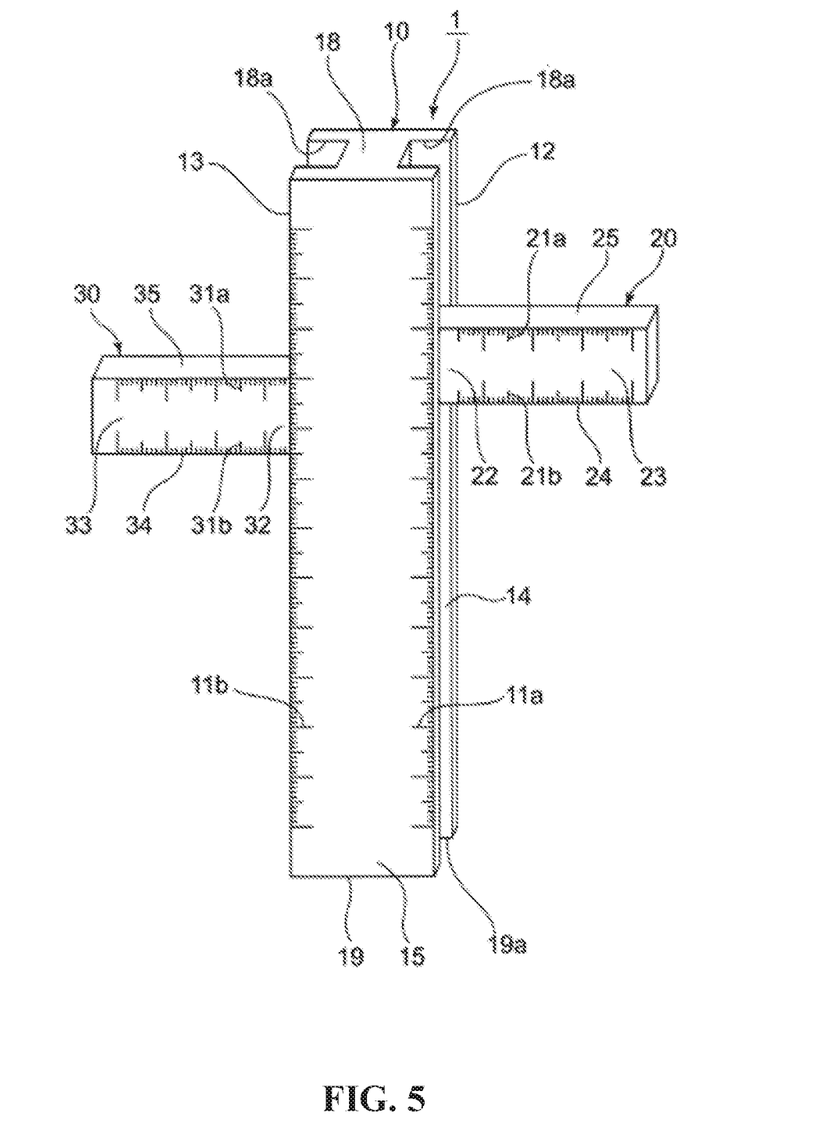
FIG. 5 is a perspective illustration showing another embodiment of a scapulae position measurement device.
Figure 6:
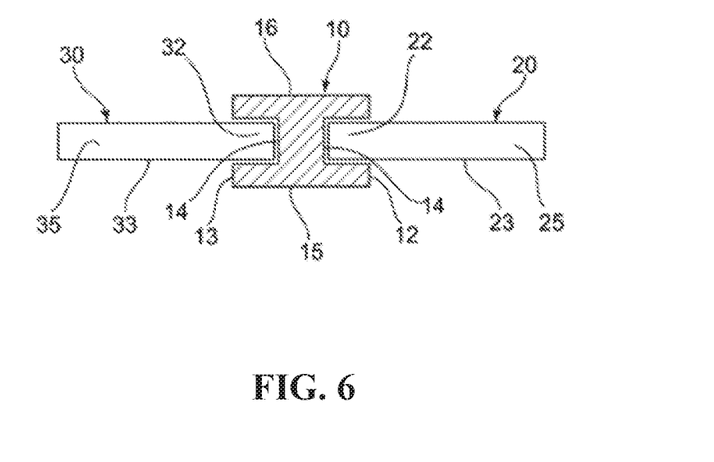
FIG. 6 is a transverse section of the scapulae position measurement device of FIG. 5.

As shown in FIG. 5 and FIG. 6, in the scapulae position measurement device 1, a groove 14 is provided from the upper edge to the lower edge of the main body 10, and this groove has an opening at the upper surface 18 and the bottom surface 19 of the main body 10.

By inserting the right arm 20 and the left arm 30 from the opening part 18a and 19a, users can easily mount the right arm 20 and the left arm 30 at the main body 10, and it becomes possible to easily assemble the scapulae position measurement device 1.

By letting go of the right arm 20 and the left arm 30 from the opening part 18a and 19a, users can easily mount the right arm 20 and the left arm 30 at the main body 10, and it becomes possible to easily disassemble the scapulae position measurement device 1.

Note that this embodiment is not limited to the above described, and the scapulae position measurement device 1 may have a cross section as shown in FIG. 4A and FIG. 4B, for example.

Figure 7A:
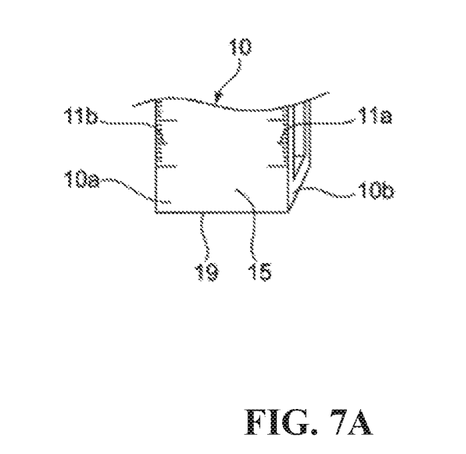
FIGS. 7A and 7B are partial perspective and bottom plan view illustrations of the main parts of an alternative embodiment of the scapulae position measurement device of FIG. 5.
Figure 7B:
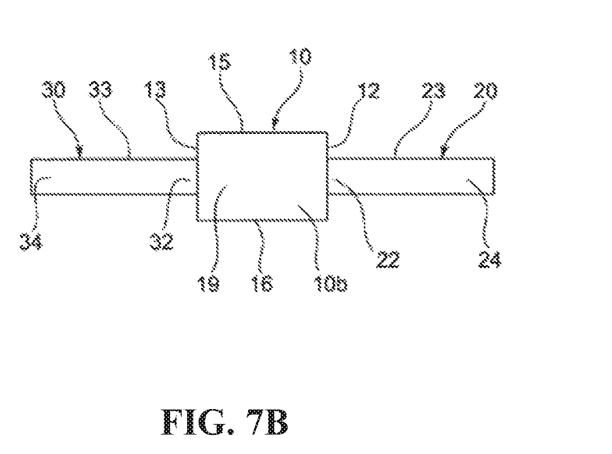

In another embodiment, shown in FIG. 7A and FIG. 7B, the scapulae position measurement device is provided with a fall-prevention device 10b to prevent the right arm 20 and/or left arm 30 from falling to the lower edge part 1 of the main body 10.

By making the groove 14 short, this fall-prevention device 10b is provided for the blocking purpose of the lower edge part 10a.

According to this, even if the right arm 20 and/or the left arm 30 falls due to gravity, the left edge part 22 of the right arm 20 and/or the left edge part 32 of the left arm 30 will be stopped at the fall-prevention device 10b which can be provided at the lower edge part 10a of the main body 10. Therefore, it is possible to prevent the right arm 20 and/or left side of the bar 30 from falling off the lower edge part 10a of the main body 10.

Note that the fall-prevention device 10b may be provided by attaching a rectangular plate to the bottom surface 19 of the main body 10.

Figure 8:
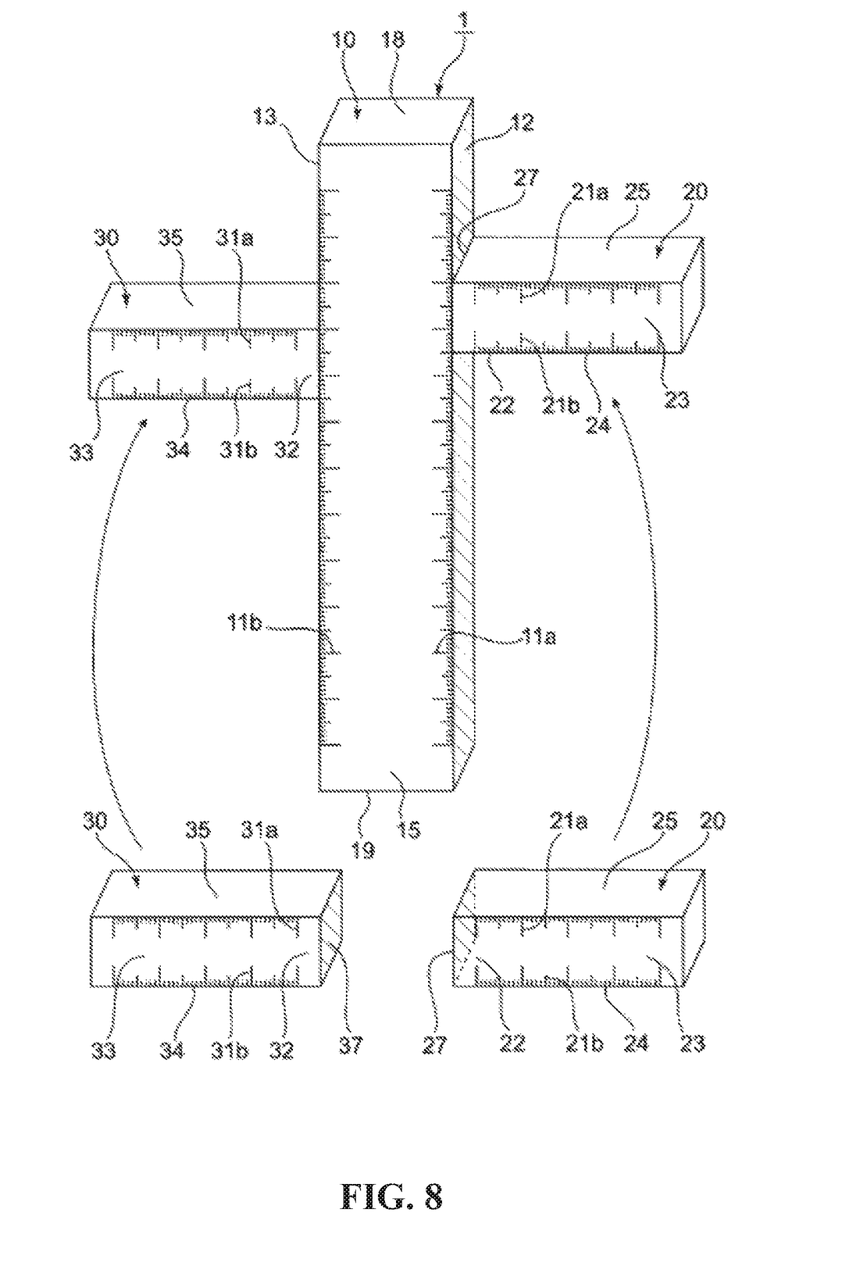
FIG. 8 is a perspective illustration of an alternative embodiment of a scapulae position measurement device.

Another embodiment of a scapulae position measurement device 1 of the present disclosure will be described while referring to FIG. 8.

In this embodiment, the main body 10 can be oriented such that the North pole of a bonded magnet is at the right side of the surface part 12 or left side of the surface part 13.

In addition, the right arm 20 can be attached to the South pole of the bonded magnet on the left side surface part 27.

The right arm 20 is detached from the right side of surface part 12 at the main body 10 by pulling the left side of surface part 27 from the right side of surface part 12 at the main body 10 and the magnetic force of the bonded magnet.

Furthermore, the left arm 30 is attached to the South pole of the bonded magnet on the right side surface part 37. The left arm 30 is detached from the left side of the surface part 13 at the main body 10 by pulling the right side of surface part 37 from the left side of surface part 13 to the main body 10 and the magnetic force of the bonded magnet.

According to this, the right arm 20 and the left arm 30 can be easily detached from the main body 10, and then, the scapulae position measurement device can easily assemble and disassemble.

Figure 9:
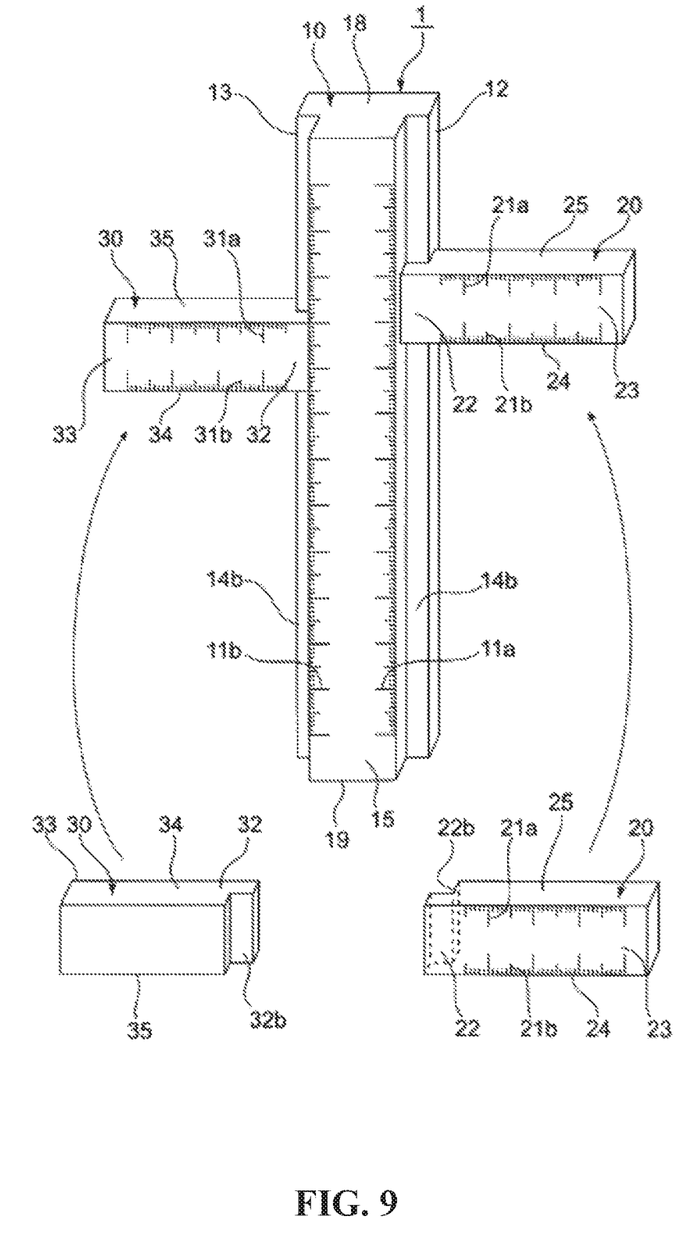
FIG. 9 is a perspective illustration showing an alternative embodiment of the scapulae position measurement device of FIG. 8.

In another embodiment, shown in FIG. 9, a shoulder 14*b* can be provided at the right side of surface part 12 and the left side of surface part 13 of the main body 10.

In addition, the right arm 20 can be provided with shoulder 14*b* of the main body 10 to fit the shoulder 22*b* at the left edge part 22. By fitting the shoulder 22*b* with the shoulder 14*b* of the main body 10, this right arm 20 will be stable when the direction and position are attached to the main body 10.

In addition, the left arm 30 can be provided with shoulder 14*b* of the main body 10 to fit the shoulder 32*b* at the right edge part 22. By fitting the shoulder 32*b* with the shoulder 14*b* of the main body 10, the right arm 20 will be stable when the direction and position are attached to the main body 10.

According to this, by stabilizing the right arm 20 and the left arm 30 when attached to the main body 10, the measurement accuracy can be improved. Also, users can easily measure the scale because the scale 21*a*, 21*b*, 31*a*, 31*b* are always oriented toward the front, toward the face of the users.

Figure 10:
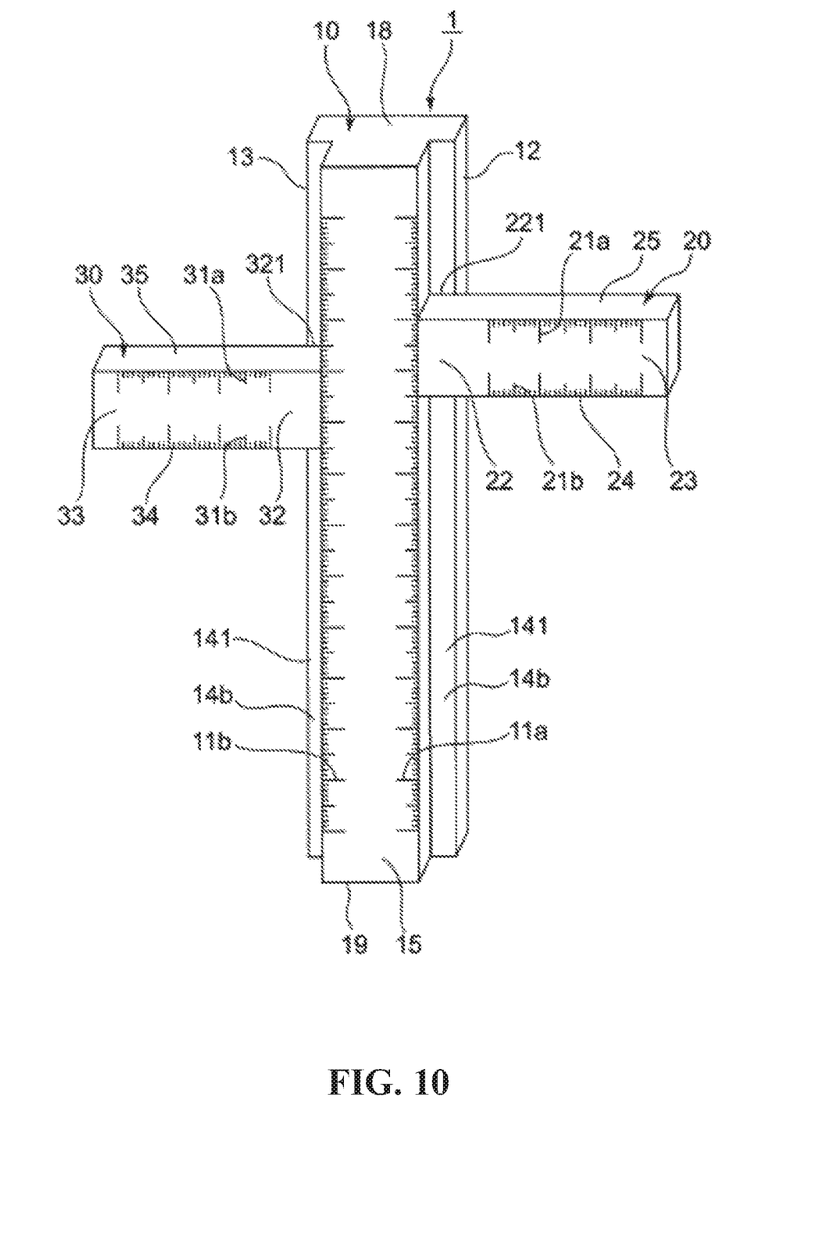
FIG. 10 is a perspective illustration showing another an alternative embodiment of the scapulae position measurement device of FIG. 8.

In another embodiment, shown in FIG. 10, a shoulder 14*b* can be provided at the right side of surface part 12 and the left side of surface part 13 of the main body 10.

In addition, the right arm 20 is a rectangular pillar material, and the back surface part 221 of the left edge part 22 is leaning on the front surface 141 of the shoulder 14*b* at the main body 10. By leaning the back surface 221 of the left edge part 22 to the front surface 141 of the shoulder 14*b* at the main body 10, the right arm 20 will be stable when the direction and the position are attached to the main body 10.

In addition, the left arm 30 is a rectangular pillar material, and the back surface part 321 of the right edge part 32 is leaning on the front surface 141 of the shoulder 14*b* at the main body 10. By leaning the back surface 321 of the right edge part 32 to the front surface 141 of the shoulder 14*b* at the main body 10, the left arm 30 will be stable when the direction and the position are attached to the main body 10.

According to this, by stabilizing the right arm 20 and the left arm 30 when attached to the main body 10, the measurement accuracy can be improved. Also, users can easily measure the scale because scale 21*a*, 21*b*, 31*a*, 31*b* are always oriented toward the front, to face the users.

Figure 11:
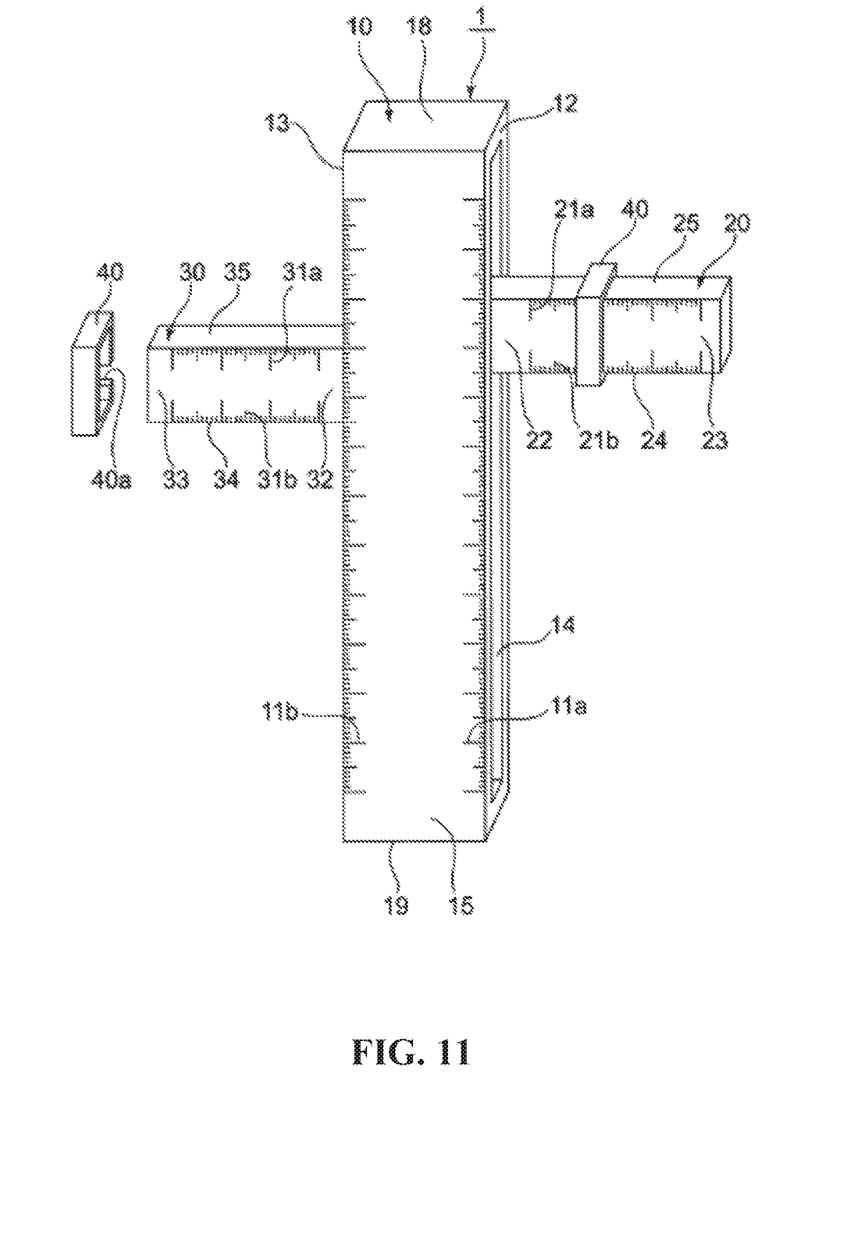
FIG. 11 is a perspective illustration of another alternative embodiment of a scapulae position measurement device.

Another embodiment of a scapulae position measurement device 1 of the present disclosure will be described while referring to FIG. 11.

By sliding the right arm 20 and/or left arm 30 in the horizontal direction, the scale indicator material used for the indicator member 40 will indicate the scale reading.

The scale indicator material used for the indicator member 40 can completely or partly encircle the respective arm 20 or 30, and the right arm 20 or the left arm 30 can be configured to fit the shape and size of the internal surface of the indicator member 40. The scale indicator material used for indicator member 40 can have an opening part 40*a* at the back surface side, and the opening part 40*a* can be smoothly slid in the horizontal direction by widening it. This scale indicator material used for indicator member 40 can be configured to have a width (length of the horizontal direction) of about 0.3-1.0 cm.

According to this, by sliding the scale indicator material used for the indicator member 40 to the position of the reading scale, the scale 21*a*, 21*b*, 31*a*, 31*b* of the right arm 20 and/or left side of the arm can be measured easily.

Figure 12A:
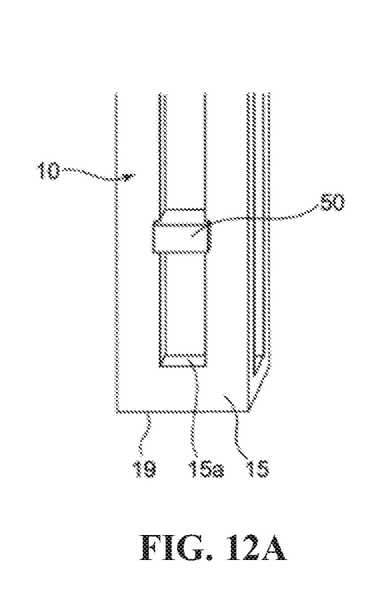
FIGS. 12A and 12B are partial perspective illustrations of an alternative embodiment of the scapulae position measurement device of FIG. 11.

In another embodiment, shown in FIG. 12A, the scapulae position measurement device 1 can have a vertical groove 15*a* at the front surface 15 of the main body 10, and a main body scale indicator member 50 fitted in the groove 15*a*. The main body scale indicator member 50 can be slid within the groove 15*a* in the vertical direction, and the scale readings will be indicated.

Figure 12B:
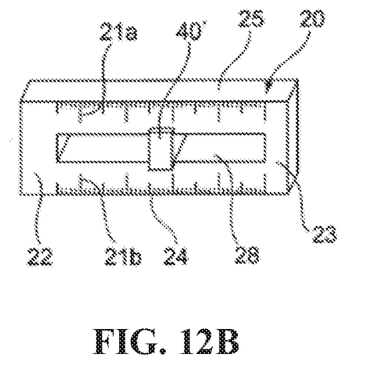

In another embodiment, shown in FIG. 12B, the scapulae position measurement device 1 can be provided with a groove 28 in the horizontal direction at the front surface 23 of the right arm 20, and the scale indicator material used for the indicator member 40 fitted to groove 28. The scale indicator material used for the indicator member 40 slid with groove 28 in the horizontal direction, and the scale readings will be indicated. Note that, the scale indicator material used for the indicator member 40 can also be used for the left arm 30.

Figure 13:
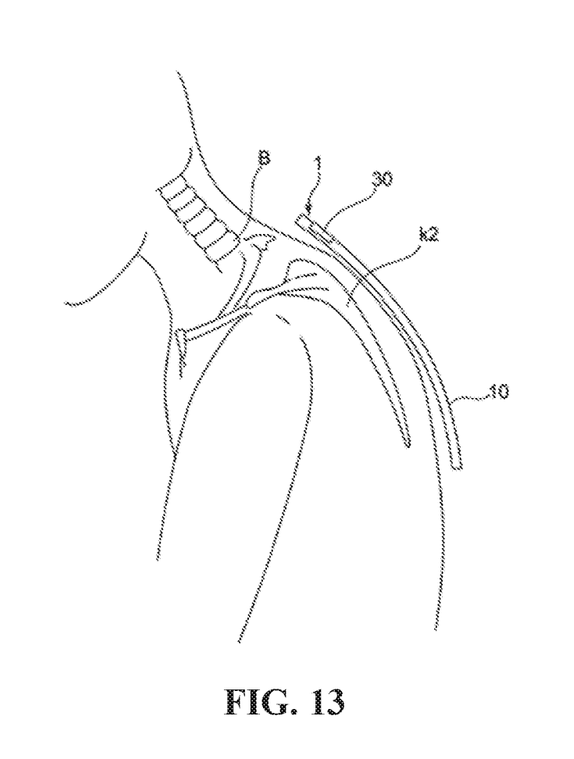
FIG. 13 is a side view of another alternative embodiment of a scapulae position measurement device.

Another embodiment of a scapulae position measurement device 1 of the present disclosure will be described while referring to FIG. 13.

The main body 10 is formed of a material that is flexible with respect to its thickness.

According to this, even when the test subject is a person whose back is bent due to an incident such as a traffic accident, the main body 10 can be bent together with the spinal column B. Due to this, even when the test subject is a person whose back is bent, the position of the predetermined location of the scapula can be measured.

Another embodiment of a scapulae position measurement device 1 according to the present disclosure will be described while referring to FIG. 14.

Figure 14:
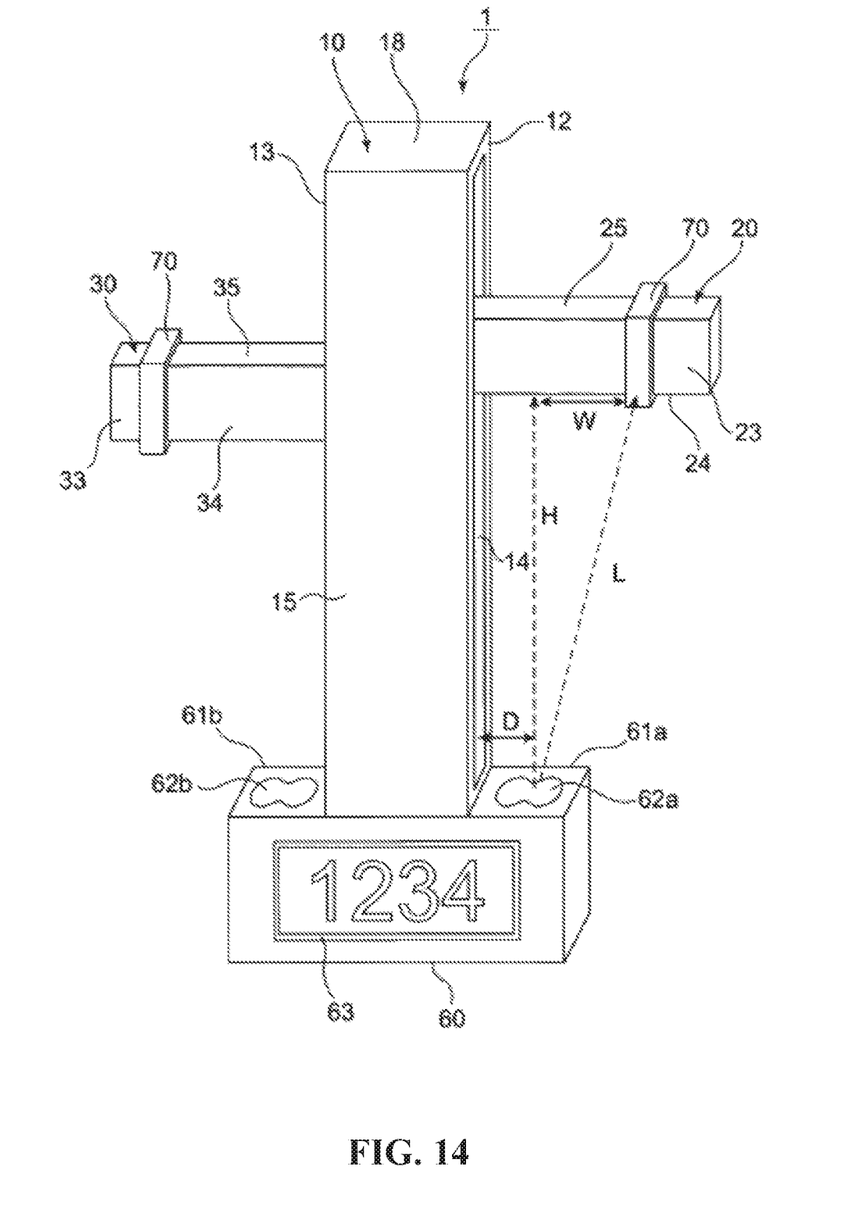
FIG. 14 is a perspective illustration of an alternative embodiment of a scapulae position measurement device.

As shown in FIG. 14, the scapulae position measurement device 1 includes the laser distance meter 60 as a positional measurement device at the lower edge part of the main body 10. By projecting the laser distance meter 60 to both sides of the right side and left side from the main body 10, the upper surfaces 61*a* and 61*b* of the distance meter 60 will be formed at the right side and left side of the main body 10. This includes having the right side of the sensor part 62*a* to the right side of the upper surface 61*a* and the left side of the sensor part 62*b* to the left side of the upper surface 61*b* together with the measurement value display part 63 at the front surface.

The right arm 20 and/or left arm 30 can include an indicator member 70, which can slide upon the respective arm horizontally to indicate the measurement position.

First of all, the laser distance meter 60 will have the right side of the sensor part 62*a* to measure the position of the vertical direction at the right arm 20, and then measure the position of the vertical direction in a predetermined location at the right scapulae, and measure the distance L up to the indicator member 70 of the arm at the right arm 20. Next, from the Pythagorean theorem, based on the distance L and position H, the laser distance meter 60 will calculate the distance W of the horizontal direction from the right side of the sensor 62*a* up to the indicator member 70 of the arm, and then, by adding or subtracting the distance D and the distance W from the right side of the surface part 12 at the main body 10 which can be stored beforehand, the position of the horizontal direction in the predetermined location at the right scapulae will be measured.

Similarly, the laser distance meter 60 will first have the left side of the sensor part 62*b* to measure the position of the vertical direction at the left arm 30, and then measure the position of the vertical direction in a predetermined location at the left scapulae, and measure the distance L up to the indicator member 70 for the left arm 30. Next, from the Pythagorean theorem, based on the distance L and position H, the laser distance meter 60 will calculate the distance W of the horizontal direction from the left side of the sensor 62*b* up to the indicator member 70 for the arm, and then, by adding or subtracting the distance D and the distance W from the left side of the surface part 13 at the main body 10 which can be stored beforehand, the position of the horizontal direction of the predetermined location at the left scapulae will be measured.

Finally, the laser distance meter 60 will present the position of the vertical direction and the position of the horizontal direction of the predetermined location which have been measured at the right scapulae and the measurement value of the position of the vertical direction and position of the horizontal direction of the predetermined location at the left scapulae at the measurement value display part 63.

Note that, the laser distance meter 60 may analyze and manage measurement values, which can be calculated after sending data to a computer, whereby the display can be skipped.

In addition, the laser distance meter 60 may be fixed at the main body 10, and may be provided with a detachable form at the main body 10. Especially, if the laser distance meter 60 at the main body 10 is provided with a detachable form, the assembling work can be carried out at the measurement area and it will be convenient as the data can be stored, such as on a portable compact disk.

In addition, the laser distance meter 60 will also measure the angle θ in the rotation state at the scapulae based on each of the values described above, and the angle θ of the scapulae may be presented at the measurement value display part 63.

In addition, the positional measurement device is not only limited to the laser distance meter, and may also take measurements such as distance etc. electrically, optically or ultrasonically. The position of the horizontal direction and the position of the vertical direction with a predetermined location may be measured at the right or left scapulae.

Note that, the above mentioned implementation forms for each right arm 20 and each left arm 30 will be provided to both sides of the main body 10, but one arm may provide as the matter to either one side of the main body 10. For this case, after changing the position of the arm at the right side of the main body 10, a user can measure the position of the horizontal direction and the vertical direction of the predetermined location at the right scapulae. The position of the similar arm will be changed to the left side of the main body 10 and the measuring methods for the position of the horizontal direction and vertical direction of the predetermined location at the left scapulae can be mentioned.

As described above, the figure surface will be referred and the implementation form of the present invention can be described but the present invention is not limited to the illustrated implementation form. It is possible to add various modifications and variations in the present invention and within the same range, or within the equivalent range to the illustrated implementation form.

What is claimed is:

1. A scapula position measurement method for use with a person having right and left scapulae, comprising:
    positioning a main body of a scapula position measurement device vertically in a predetermined location along a spine of the person;
    moving a right horizontal arm, extending from a side of the main body, to align with an upper corner of the right scapula of the person;
    determining an upper horizontal position of the upper corner of the right scapula by measuring a position of the upper corner of the right scapula relative to the right horizontal arm;
    determining an upper vertical position of the upper corner of the right scapula by measuring a position of the right horizontal arm relative to the main body;
    moving the right horizontal arm to align with a lower corner of the right scapula;
    determining a lower horizontal position of the lower corner of the right scapula by measuring a position of the lower corner of the right scapula relative to the right horizontal arm;
    determining a lower vertical position of the lower corner of the right scapula by measuring a position of the right horizontal arm relative to the main body;
    moving a left horizontal arm, extending from a side of the main body, to align with an upper corner of the left scapula of the person;
    determining an upper horizontal position of the upper corner of the left scapula by measuring a position of the upper corner of the left scapula relative to the left horizontal arm;
    determining an upper vertical position of the upper corner of the left scapula by measuring a position of the left horizontal arm relative to the main body;
    moving the left horizontal arm to align with a lower corner of the left scapula;
    determining a lower horizontal position of the lower corner of the left scapula by measuring a position of the lower corner of the left scapula relative to the left horizontal arm; and
    determining a lower vertical position of the lower corner of the left scapula by measuring a position of the left horizontal arm relative to the main body.

2. A scapula position measurement method in accordance with claim 1, wherein determining the upper or lower horizontal position of the right or left scapulae comprises comparing the position of the upper or lower corner of the respective scapulae relative to a horizontal scale disposed upon the respective left or right horizontal arm.

3. A scapula position measurement method in accordance with claim 1, wherein determining the upper or lower vertical position of the right or left scapulae comprises comparing the position of the respective left or right horizontal arm, when aligned with the upper or lower corner of the respective scapulae, relative to a vertical scale disposed upon the main body.

4. A scapula position measurement method in accordance with claim 1, wherein determining the upper and lower horizontal and vertical positions of the right or left scapulae comprises measuring the position of the predetermined location with respect to the respective left or right horizontal arm and measuring the position of the respective left or right horizontal arm with respect to the main body using a positional measurement device disposed upon the main body, and an indicator member positioned upon each of the left and the right horizontal arms.

\* \* \* \* \*